(12) United States Patent
Graumann et al.

(10) Patent No.: US 8,699,670 B2
(45) Date of Patent: Apr. 15, 2014

(54) METHOD FOR GEOMETRICALLY CORRECT ASSOCIATION OF 3D IMAGE DATA OF A PATIENT

(75) Inventors: Rainer Graumann, Hoechstadt (DE); Gerhard Kleinszig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 43 days.

(21) Appl. No.: 13/451,983

(22) Filed: Apr. 20, 2012

(65) Prior Publication Data
US 2012/0281808 A1 Nov. 8, 2012

(30) Foreign Application Priority Data
Apr. 20, 2011 (DE) .......................... 10 2011 007 794

(51) Int. Cl.
*H05G 1/28* (2006.01)
(52) U.S. Cl.
USPC .......................................... 378/162; 378/901
(58) Field of Classification Search
USPC ..................... 378/4, 162, 163, 901
See application file for complete search history.

(56) References Cited

U.S. PATENT DOCUMENTS 6,561,695 B2 * 5/2003 Proksa .......................... 378/207
2011/0093108 A1 4/2011 Ashby et al.

FOREIGN PATENT DOCUMENTS

EP 1 632 181 3/2006

OTHER PUBLICATIONS

"Image Fusion for Intraoperative Control of Axis in Long Bone Fracture Treatment" Messmer et al., European Journal of Trauma, vol. 6 (2006) pp. 555-561.

* cited by examiner

*Primary Examiner* — Jurie Yun
(74) *Attorney, Agent, or Firm* — Schiff Hardin LLP

(57) ABSTRACT

In a method for geometrically correct association of at least two 3D image data of a patient, a marker field that defines a reference and is dimensionally stable and can be imaged in an x-ray image, is fixed in a stationary position relative to the patient. An x-ray apparatus is brought into first and second 3D acquisition positions. In each of the 3D acquisition positions, the x-ray apparatus acquires first 2D x-ray images for the associated 3D image data in various positions. The first and second 3D acquisition positions are selected such that a second 2D x-ray image that includes an image of at least a portion of the marker field is acquired in at least one respective position. The respective attitudes of the 3D acquisition position and the 3D image data in the reference system are determined from the image of the marker field in the second 2D x-ray image. First and second image data are geometrically correctly associated with one another according to their respective attitude.

6 Claims, 2 Drawing Sheets

METHOD FOR GEOMETRICALLY CORRECT ASSOCIATION OF 3D IMAGE DATA OF A PATIENT

BACKGROUND OF THE INVENTION

1. Field of the Invention

The present invention concerns a method in which at least two 3D image data items of a patient are geometrically correctly associated with one another.

2. Description of the Prior Art

In the operative treatment of fractures of long hollow bones, care must be taken that the corresponding extremity axes of the patient are established in the original form. For example, in the case of a femur fracture the leg axis (avoiding varus or valgus alignment), the leg rotation and the leg length must be set correctly.

It is known to visually check the leg axis interoperatively with an auxiliary means. The cable of an electrocauterization tool is often used for this purpose. It is also known to measure the leg length in comparison to the healthy leg of the patient and to visually compare the leg rotation with the healthy leg.

A 3D x-ray method and apparatus (for example a 3D x-ray C-arm) are often employed intraoperatively. Such a method or apparatus generates a 3D image data set of the patient in the form of a reconstructed spatial region (shortened in the following to "3D image data"). For acquisition, the apparatus is fixed in a 3D acquisition position. For example, for the aforementioned C-arm a basic support is fixed at a specific spatial position in the operating room (OP). The x-ray apparatus is moved between different positions in this invariant basic alignment. For example, in the case of the aforementioned C-arm the C-arm of the apparatus is moved orbitally between different positions with an immobile basic support. A set of 2D x-ray images or 2D projection images is thus acquired from which the 3D image data are then reconstructed.

Such 3D (normally mobile) x-ray apparatuses that can be used intraoperatively most often have a relatively small reconstruction volume for the 3D image data, for example a cube with edges of only 15 cm in length. The volume is directly coupled to the size of the x-ray detector that is used. A long hollow bone is multiple times longer, so that multiple 3D image data of the patient must be acquired in order to image the entire bone. Newer methods enable the geometrically correct composition of individual 3D image data into a complete 3D image from which the leg axis and the leg length can be derived.

"Geometrically correct" means that, with regard to the imaged patient, the non-contiguous 3D image data are spatially accurately associated with one another relative to form an imaginary complete image (thus like spatial sections that are spatially fixed relative to one another). They thus depict the real relationships to the patient with spatial accuracy through their mutual attitude and orientation. The partial volumes can be contiguous (i.e. overlap), but need not be, in order to image a larger patient volume as a whole.

There are two approaches for combination ("stitching") of the 3D image data. In the first approach, multiple 3D image data are acquired with overlapping of respective images or spatial regions that are sufficient in pairs in order to generate contiguous 3D image data from these. Image fusion algorithms are used for this purpose.

In the second approach, the individual 3D image data are acquired so as to not overlap; for example, first 3D image data of the hip, second of the knee and third of the ankle of the same patient are acquired. Due to the lack of overlap, however, here a uniform reference system or coordinate system must be achieved for all (partial) data sets (thus 3D image data) in order to geometrically correctly arrange the individual 3D image data or bring them into congruence. For example, here the respective position determination of the imaging system using a commercially available tracking (i.e. position detection) system would be conceivable. However, this requires additional hardware and software cost and therefore is hard for the user to accept.

There are numerous possibilities for realization for the stitching or other correct spatial association methods in the 2D field. For example, a rigid marker plate with x-ray-visible markers (location codes) for the spatial association of 2D x-ray images is known from the article "Image Fusion for Intraoperative Control of Axis in Long Bone Fracture Treatment", Peter Messmer et al., European Journal of Trauma 2006, No. 6, P. 555-561, Urban & Vogel. The marker plate is placed beneath the patient so that parts of this are visible in multiple partial 2D x-ray images (also not overlapping). The marker plate enables a geometrically correct association of the 2D individual images with one another since the x-ray-visible location codes of the marker plate are visible in the x-ray image and allow the association.

The marker plate must be placed below the patient before his positioning; a later placement is therefore no longer possible. The marker plate must be positioned and also cleaned in the operating room. Under the circumstances, the marker plate disruptively presses through the patient bed.

This approach fails for intraoperative 3D imaging with the aforementioned small reconstruction volume since the distances between marker plate and a location of interest in the patient that is to be imaged are often too large for these to be recorded in individual 3D image data.

SUMMARY OF THE INVENTION

An object of the present invention is to provide an improved method for geometrically correct association of 3D image data of a patient.

The object is achieved by a method according to the invention wherein a marker field is fixed in a stationary position relative to the patient. The marker field can be imaged in an x-ray image (thus radiographically). The marker field is dimensionally stable in the sense that it is not spatially variable relative to the patient, at least during the x-ray acquisitions made within the scope of the method. The marker field defines a reference system, i.e. a coordinate system for a later coordinate association.

An x-ray apparatus is successively brought into first and second 3D acquisition positions. In each of the 3D acquisition positions the x-ray apparatus occupies different positions in turn. In each position, the x-ray apparatus acquires a first 2D x-ray image. All 2D x-ray images generated in the respective 3D acquisition position ultimately supply the associated first and second 3D image data for the first and second 3D acquisition position.

Moreover, the first and second 3D acquisition positions are selected such that a second 2D x-ray image of the x-ray apparatus can be acquired in at least one respective position in the selective 2D acquisition position. The selection occurs so that at least a portion of the marker field is imaged in the 2D x-ray image. The respective first and second 3D acquisition positions can now be determined in relation to the reference system, and therefore also the respective attitude of the 3D image data in the reference system. According to their respective attitude in the reference system, the first and second 3D image data can subsequently be geometrically correctly associated with one another in the reference system.

By means of the associated projection matrices, the center points and directions of the reconstruction volumes can be determined in the coordinate system of the marker plate from the positions of the x-ray markers in the second 2D x-ray images. The angle of inclination of the reconstructed volumes can be calculated from the evaluation of the imaged areal extent of the marker system (marker plate) in the projection images. It is thereby possible to transfer the independent coordinate systems of the individual reconstructed volumes (thus 3D image data) into a global coordinate system—the reference system of the marker plate. The individual volumes can then be presented in a single coordinate system. For example, after setting fractures leg axes can be determined much more precisely from this than with just the 2D projection methods. Determinations of the leg rotation are likewise possible, which is only possible only in a rudimentary fashion by means of 2D.

The marker field is provided so that a respective imaging (of a portion) of the marker field in the x-ray image allows a determination of the position of the x-ray apparatus relative to the marker field. The geometric relationship of the x-ray images to one another can be determined from the geometric relationship of the x-ray images that is known via the marker field.

For example, with OP tables or acquisition apparatuses positioned at an angle an acquisition situation results in which the marker field is imaged in the exposures from a direction inclined relative to their plane. The acquisition angle can then be determined from the distortion [sic] image of the marker field. For example, a quadratic image section then appears as a distorted trapezoid or rhombus in the corresponding exposure or, respectively, image.

The method according to the invention that is explained in the context of an x-ray application can also be transferred to other radiographic methods, for example magnetic resonance tomography or 3D ultrasound imaging, and therefore is not limited only to x-ray applications. It need only be ensured that the marker plate is imaged in a respective 3D acquisition position via an additional acquisition (not necessarily connected with the 3D reconstruction), and that the 3D acquisition position (and therefore the 3D attitude) of the 3D image data can be determined from this. For non-projective methods such as MR or ultrasound, however, the method cannot be transferred one to one since these do not operate with projections, and therefore information from outside of the reconstructed region does not exist.

According to the invention, the problem of volume stitching in a 3D region with non-overlapping spatial regions of the 3D image data is solved by two-dimensionally distributed x-ray markers, or even line-shaped marker structures, being attached in the form of the marker field in the acquisition region of the x-ray apparatus. The x-ray markers thereby form an unambiguous code in which an imaging of the marker allows an unambiguous association of the associated acquisition position in space. According to the invention, the x-ray markers do not need to be included in the 3D reconstruction volume. In order to be able to determine the marker positions in 3D, it is entirely sufficient if the markers are visible in at least two or a few of the x-ray projection images used for 3D volume generation.

The basis of the invention lies in the use of 2D marker structures for the 3D stitching of non-overlapping regions, wherein the markers do not need to be included in the reconstructed 3D volumes, which leads to a very simple realization. A very simple method advantageously results for stitching of non-overlapping 3D volumes and without use of additional position detection systems. The system can be realized wholly automatically and without additional user interaction.

In a preferred embodiment, the marker field is arranged outside of the spatial region associated with the 3D image data. The marker field or its image does not distort the 3D image data itself when the 3D marker field lies outside of the reconstruction volume. At most, artifacts are hereby generated that interfere with the 3D imaging but are tolerable or can even be eliminated.

In a preferred embodiment, one of the first 2D x-ray images is used as a second 2D x-ray image. A second 2D x-ray image in the actual sense therefore does not need to be acquired again. The respective first x-ray exposure is also used again as a second x-ray exposure (thus twice): on the one hand for reconstruction of the 3D image data, on the other hand for spatial determination of the 3D acquisition position in the reference system.

In a further preferred embodiment, the patient is arranged on an OP table. The marker plate is then fixed on the OP table. For example, the marker plate is placed on the OP table and the patient is laid on the marker field. Since a 3D x-ray apparatus is operated at least once with the x-ray source in an over-table position and the detector in an under-table position (or vice versa) in the 3D acquisition, it is ensured that the second 2D x-ray acquisition also images the marker field as well in at least this position. The marker plate can also be attached to the side of the table before the acquisition and be removed after the acquisition.

In a further preferred embodiment, the marker field is arranged so that this can be removed and/or affixed without repositioning the patient. The marker field can be removed (for example after a second x-ray image has been produced to determine the 3D acquisition position in the reference system) in order to not interfere with the 3D image data generated in the same acquisition position.

For example, the following procedure is conceivable: [sic] is initially produced free of artifacts in a first 3D acquisition position without marker field. The marker field is introduced. In the first acquisition position, a second 2D x-ray image is produced to determine attitude in a reference system. The x-ray apparatus is shifted into the second 3D acquisition position. There a second x-ray image is produced again to determine attitude of the second 3D acquisition position in a coordinate system. The marker field is removed and second 3D image data are generated in the same second acquisition position. Two artifact-free 3D volumes are thus provided which nevertheless can be geometrically associated with one another with spatial accuracy in a reference system of the marker plate.

In a preferred variant of this embodiment, the marker field is arranged and affixed within or below the patient table. For example, the marker field is arranged in an intervening space between the top side on which the patient lies and the underside of the patient table.

In a further preferred embodiment, a foil is used as a marker field and this is affixed so as to be dimensionally stable. Although the foil is in fact normally not dimensionally stable, this is affixed at least for the acquisition of the two second 2D x-ray images so that it remains at rest without spatial variation. For example, the dimensional stability is achieved by guidance of the foil, for example by placement of the foil on a dimensionally stable surface or holding the foil under tensile stress.

In other words, it is thus proposed to place x-ray markers on a flexible foil. This foil can be introduced or removed again below the OP table in a guide as needed. It is therefore ensured that the marker structures are only visible in the x-ray images when they are also necessary. The flexible marker foil is unrolled below the table from a roll attached to the OP table and is affixed at the other end of said OP table. The foil can either be retracted to the roll after use, or can be cut and discarded. An easy suspension of the foil in the z-direction is hereby not relevant, for example if the precision requirements of the association of the 3D image data relate to an x-direction and y-direction. For example, this is provided given an axis or length determination at a leg.

A sterilization of the foil is then not necessary since it is located below the OP table; a normal OP-specific cleaning is therefore sufficient. A flexible and arbitrarily positionable marker system is thus realized via the foil. The marker system can be used in the OP corresponding to the clinical application. The foil is used in the measurement of axes and lengths at the patient and in the acquisition of high-resolution measurements; for example, the foil can be removed for detail acquisitions so that the marker structures do not interfere with the 3D reconstruction.

In an alternative embodiment of the method, the marker field is affixed to the patient as a rigid plate. For example, the rigid plate is placed on the body part of the patient that is to be radiographed (his upper thigh, for example); the patient hereby lies on an operating table, for example.

In a further embodiment of the method, the patient is placed on a top side of a patient table and the marker field is attached to the underside of the patient table, opposite the patient.

In one variant of this embodiment, the marker field is mounted flat on the underside. For example, the marker field then covers the entire table region (in the viewing direction orthogonal to the table) in which patient regions to be imaged can be borne.

In a further variant of this embodiment, the marker field is therefore attached so that it covers an entire region of the patient table that is considered for the passage of x-ray radiation to produce the x-ray exposures.

In a preferred embodiment, the marker field is a sequence of respectively different, optically detectable figures in pairs whose respective spatial position is known relative to the marker field. In other words: each figure represents an unambiguously identifiable spatial identifier which allows the aforementioned geometric association. An image of a portion of the marker field is therefore unambiguously identifiable in terms of its position within the marker field. In the event that optically visible markers are used exclusively, a video camera must be used (for example connected to the C-arm) that has a known spatial position relative to the radiator or, respectively, detector, for example. This is an extension of what is known as the CAMC principle.

In a preferred embodiment of this variant, each figure includes a bar code that indicates the respective spatial position of the figure in the marker field. The bar code is a 2D or, respectively, n×n bar code, for example; the spatial or, respectively, relative position is a 2D position in a flat marker field, otherwise a spatial position given a spatially curved or expanded marker field, for example.

In an alternative embodiment of the method, the marker field is attached permanently to the patient table, in particular as explained above. The required relative spatial fixing between marker field and patient position always results, in particular given a patient resting on the patient table.

DESCRIPTION OF THE PREFERRED EMBODIMENTS

Figure 1:
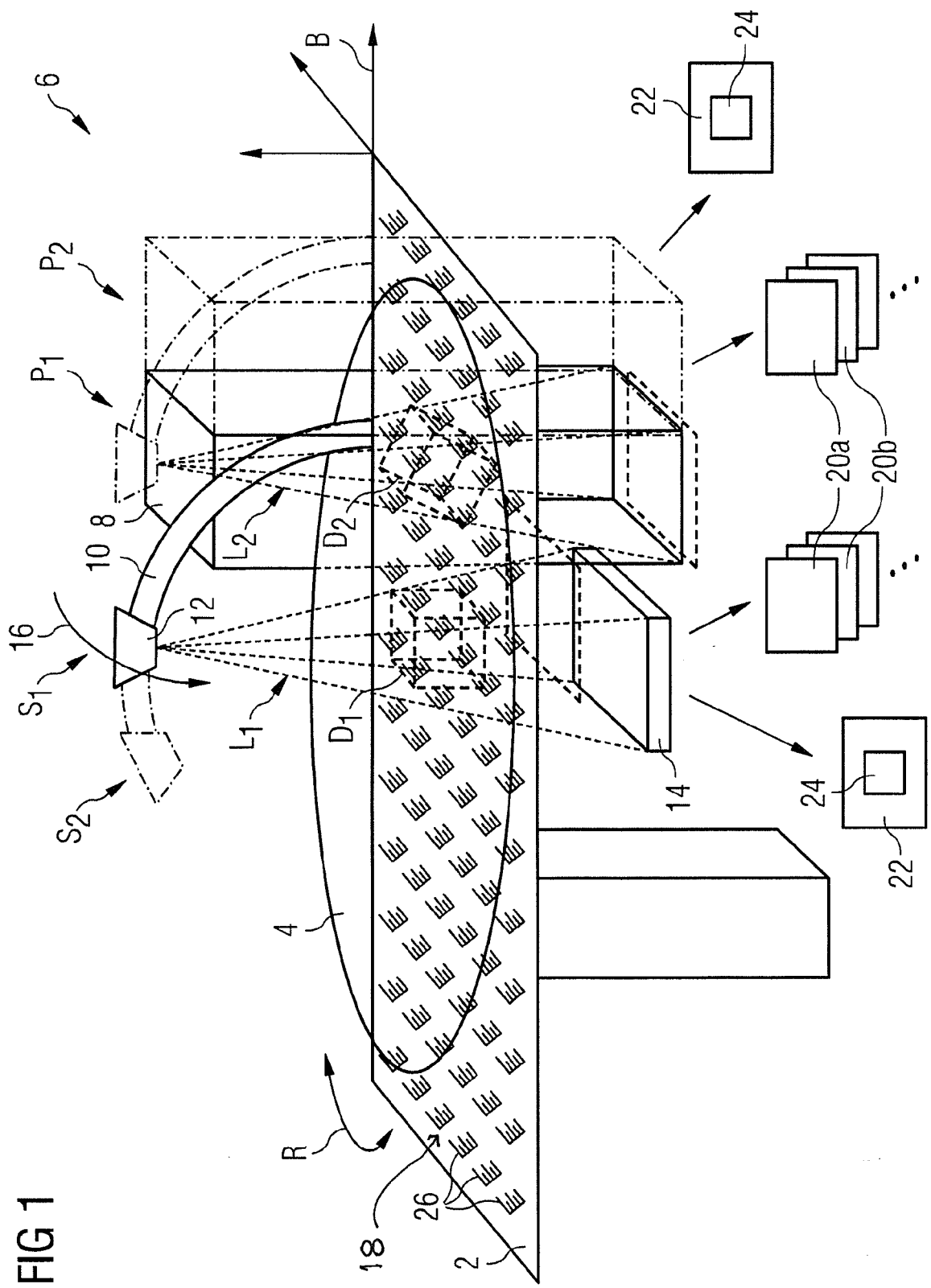
FIG. 1 shows an x-ray system with 3D image data of a patient.

FIG. 1 shows a patient table 2 with a patient 4 borne on it, on which patient a medical procedure is to be implemented. The procedure should take place with x-ray monitoring. FIG. 1 therefore also shows an x-ray apparatus 6, in the exemplary embodiment a 3D x-ray C-arm. The x-ray apparatus 6 has a basic support 8 on which a C-arm 10 is supported. The C-arm 10 has an x-ray source 12 and an x-ray detector 14 mounted thereon. The C-arm 10, together with the x-ray source 12 and the x-ray detector 14, can be moved orbitally relative to the basic support 8, in or counter to the direction of the arrow 16. A marker field 18 is placed between the patient table 2 and the patient 4 on the patient table 2. The marker field 18 is therefore at rest in a fixed relative position R relative to the patient 4. The marker field 18 defines a reference system B.

FIG. 1 shows the x-ray apparatus 6 in solid lines in a first 3D acquisition position P1. In this 3D acquisition position the basic support 8 is spatially fixed relative to the patient 4. Only the C-arm 10 moves in or counter to the direction of the arrow 16 between different positions S1, S2, ... (shown in a dashed line in FIG. 1). A first 2D x-ray image 20a, 20b, ... of the patient 4 is respectively acquired at each of the positions S1, S2, ... All first 2D x-ray images 20a, 20b, ... generated in the 3D acquisition position P1 are associated with this position P1 and serve for the reconstruction of first 3D image data D1 likewise associated with the 3D acquisition position P1. A second 2D x-ray image 22, which depicts at least a portion of the marker field 18, is additionally acquired in the same 3D acquisition position P1 at one of the positions S1, S2, ..., or an arbitrary other position that is spatially known relative to these positions S1, S2, ... The first 3D acquisition position P1 is selected so that the marker field 18 can also be imaged in at least one position of the x-ray apparatus 6 in the second x-ray image 22.

In an alternative embodiment, one of the first 2D x-ray images 20a, 20b, ... can be used as a second x-ray image 22.

The attitude L1 of the 3D image data D1 in the reference system B is determined from an image 24 of the marker field 18 in the second 2D x-ray image 22 via the known imaging geometry of the x-ray apparatus 6.

The x-ray apparatus 6 or the basic support 8 thereof is subsequently shifted into a second 3D acquisition position P2 (shown in dashed lines in FIG. 1). The aforementioned steps are repeated identically at position P2, meaning that here first 2D x-ray images 10a, 10b, ... are acquired at respective positions S1, S2, ... given invariant 3D acquisition position P2 in order to reconstruct second 3D image data D2. A second 2D x-ray image 22, which has a different image 24 of the marker field 18, is also generated again in the same manner in the second 3D acquisition position P2. From this image 22, the attitude L2 of the second 3D image data D2 is determined in the same manner in the reference system B.

From FIG. 1 it is apparent that the 3D image data D1, D2 lie entirely within the patient 4, whereas the marker field 18 is located outside of the patient 4. The marker field 18 therefore does not lie within the respective spatial regions associated with the 3D image data D1, D2.

In order to be able to identify the respective attitude of the images 24 in the second 2D x-ray images 22 (thus the respective sections of the marker field 18), the marker field 18 has a string of respective pairs of various FIG. 26 in pairs that can be radiographically imaged and that are differentiable. The respective spatial position of each FIG. 26 on the marker field 18 (and therefore in the reference system B) is known. FIG. 26 are therefore differentiable in pairs. The FIG. 26 are represented only symbolically in FIG. 1. The respective acquisition angle of the x-ray apparatus 6 in the production of the second 2D x-ray images 22 (thus the curve of the central x-ray beam relative to the plane of the patient table 2) is hereby reconstructed from the distorted representation of the image 24 of the respective marker structures of the marker field 18.

The marker field 18 is dimensionally stable in the sense that its attitude is invariant relative to the patient, at least in the time period between the acquisition of the two second 2D x-ray images 22 in the 3D acquisition positions P1,2.

Figure 2:
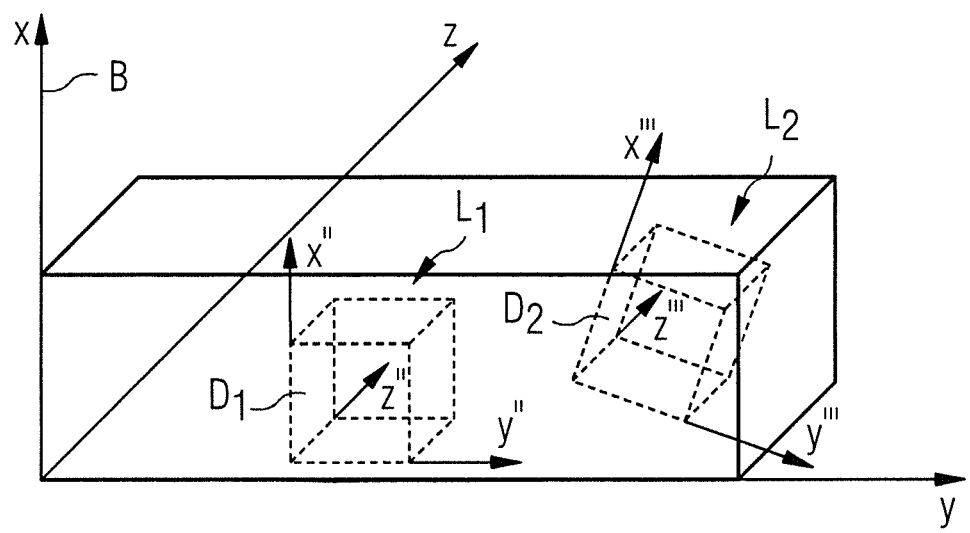
FIG. 2 shows the 3D image data associated with one another in a reference system.

FIG. 2 shows how the 3D image data D1, D2 are ultimately spatially accurately (i.e. geometrically correctly) associated with one another in the reference system B using their corresponding attitudes L1, L2.

Figure 3:
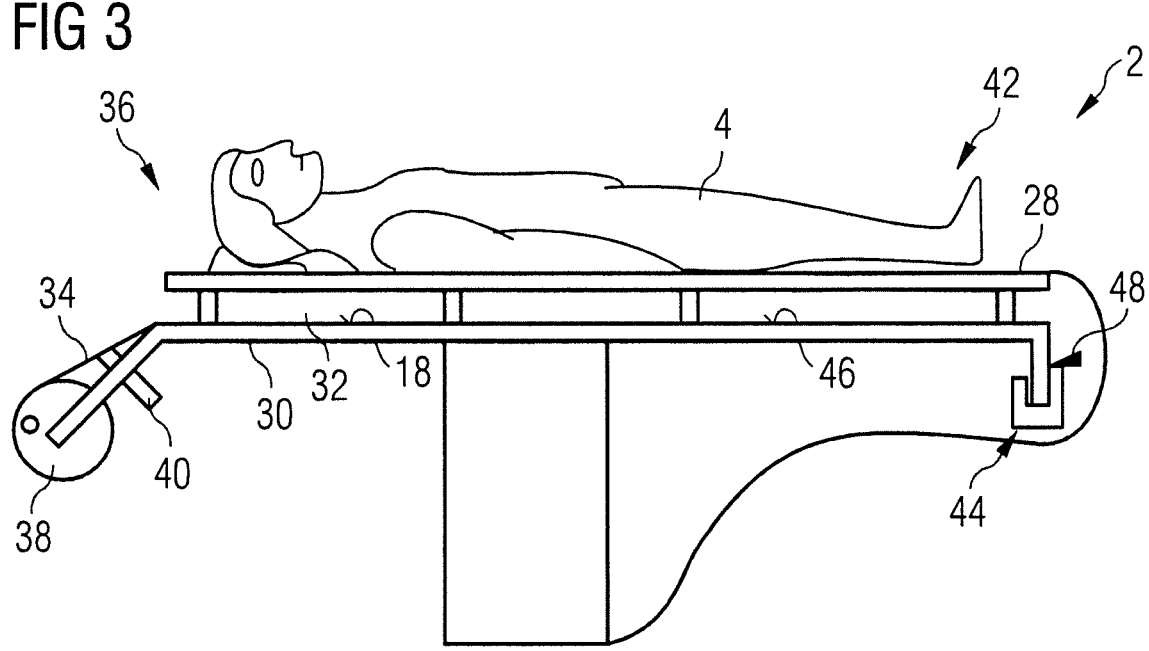
FIG. 3 shows a patient table with inset marker field.

FIG. 3 shows an alternative embodiment of a patient table 2 on whose top side 28 the patient 4 is supported. In this embodiment, the patient table 2 has an intervening space 32 arranged between its top side 28 and its underside 30. In this embodiment, the marker field 18 is arranged in the intervening space 32. Moreover, the marker field 18 here is designed as a foil 34, which is initially stored on a roller 38 at a head end 36 of the patient table 2. The foil 34 is directed via an unrolling and tensioning mechanism 40 (additionally arranged at the head end 36) and then travels through the intervening space 32 to the opposite foot 42 of the patient table 2. There it is affixed in an additional tensioning and clamping mechanism 44.

Therefore, the foil (which is inherently not dimensionally stable) is fixed in a sufficiently dimensionally stable manner, at least for the duration between the acquisitions of the two second 2D x-ray images 22. This occurs by the flat placement on the lower inner area 46 of the patient table 2. Alternatively, it would be possible to brace the foil 34 sufficiently under tension between the unrolling and tensioning mechanism 40 and the tensioning and clamping mechanism 44, with or without placement or application on a surface or other stabilization devices.

A cutting mechanism 48 mounted at the tensioning and clamping mechanism 44 serves to cut used foil 34 in order to dispose of the used foil 34.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for geometrically correctly associating at least two 3D image data items of a patient with one another, comprising:

fixing a dimensionally stable marker field at a patient table in a stationary position relative to a patient on the patient table, said stationary position being located at the patient table so as to allow said marker field to be arranged at and removed from said patient table without repositioning of said patient, said marker field defining a reference system and being visible when imaged in an x-ray image;

positioning an x-ray apparatus at a 3D selectable first acquisition position and, with said x-ray apparatus at said first acquisition position, acquiring a plurality of 2D x-ray images, which allow reconstruction of first 3D image data of the patient, respectively at a plurality of angle positions of said x-ray apparatus, and acquiring a marker field image, at at least one of said angle positions, in which at least a portion of said marker field is imaged;

moving said x-ray apparatus to a 3D selectable second acquisition position and, with the x-ray apparatus at said second acquisition position, acquiring a further plurality of 2D x-ray images, which allow second 3D image data of the patient to be reconstructed therefrom, respectively at said angle positions of said x-ray apparatus, and acquiring a further marker field image, at at least one of said angle positions, in which at least a portion of the marker field is imaged;

in a processor, from said marker field image, determining an attitude of said first acquisition position and an attitude of said first 3D image data in said reference system and, from said further marker field image, determining an attitude of said second acquisition position and an attitude of said second 3D image data in said reference system; and in said processor, geometrically correctly associating said first 3D image data and said second 3D image data with one another from their respective attitudes in said reference system.

2. A method as claimed in claim 1 comprising arranging said marker field outside of a spatial region associated with said first and second 3D image data.

3. A method as claimed in claim 1 comprising using one of said plurality of 2D x-ray images acquired with said x-ray apparatus in said first position as said marker field image.

4. A method as claimed in claim 1 comprising using one of said plurality of 2D x-ray images acquired with said x-ray apparatus in said second acquisition position as said further marker field image.

5. A method as claimed in claim 1 comprising arranging said marker field within or below said patient table.

6. A method as claimed in claim 1 comprising employing a foil having a plurality of radiopaque markers thereon as said marker field, and fixing said foil relative to said patient in a dimensionally stable manner.

* * * * *